United States Patent [19]

Esper et al.

[11] 4,356,571
[45] Nov. 2, 1982

[54] PROSTHETIC DEVICE

[75] Inventors: Friedrich Esper, Leonberg; Walter Gohl, Aidlingen, both of Fed. Rep. of Germany

[73] Assignee: Robert Bosch GmbH, Stuttgart, Fed. Rep. of Germany

[21] Appl. No.: 195,870

[22] Filed: Oct. 10, 1980

[30] Foreign Application Priority Data

Oct. 12, 1979 [DE] Fed. Rep. of Germany ....... 2941369

[51] Int. Cl.³ .............................................. A61F 1/00
[52] U.S. Cl. .......................................................... 3/1
[58] Field of Search ................ 3/1; 264/131; 525/937; 260/39 R

[56] References Cited

U.S. PATENT DOCUMENTS 4,035,550  7/1977  Suh et al. .......................... 260/39 R
4,268,468  5/1981  Esper et al. ........................ 264/131

Primary Examiner—Richard J. Apley
Assistant Examiner—David J. Isabella
Attorney, Agent, or Firm—Frishauf, Holtz, Goodman & Woodward

[57] ABSTRACT

A medical prostheses suitable for implant use comprising a cured fiber reinforced triazine resin shaped body. The fiber reinforcement is preferably a fabric formed from two dimensionally oriented fibers. The preferred fibers are high strength carbon fibers. The prosthesis is particularly useful for the fabrication of joints, for example hip joints, as well as for support and connecting elements suitable for implantation.

9 Claims, 2 Drawing Figures

PROSTHETIC DEVICE

BACKGROUND OF THE INVENTION

The present invention provides prosthetic devices utilized as implants.

It is known to use metal alloys or aluminum oxide (ceramic) as well as combinations of the two materials, as a replacement for human bones, e.g. for the hip joint. Available materials for this purpose also include metal-resin systems and also more recently developed systems utilizing carbon, for example, graphite. It is also known that metals and alloys of metals are used as support elements and also connective elements in treating bone fractures.

In both of the aforediscussed uses, the materials which have been used have exhibited disadvantages of one type or another. When replacing human bones, for example in the hip joint, the femur pin is made of metallic materials. The ball joint portion of the hip joint has preferably been prepared from metal alloys. More recently this ball joint has also been made of aluminum oxide. The socket of the hip joint has been prepared from metals as well as from aluminum oxide, and from synthetic (resin) materials or combinations of these materials. Generally bone cement is used to fix (anchor) the femur pin and the socket. Over a period of time, bone cement deteriorates and the implanted elements become loose. Recently a new means of attaching elements has been provided. However, even this new method has not been completely successful. This lack of success is attributed to the large difference in the modulus of elasticity between bones and the implanted material. A high modulus of elasticity for the implant material is disadvantageous in that, unlike bones, it does not cushion severe jolts but instead transfers them substantially without cushioning to the body. When using metals, some of the corrosion problems and abrasion problems are still present. When using aluminum oxide, it is necessary to deal with the disadvantages resulting from high sensitivity to shock.

The use of synthetic materials such as resins alone is not useful for the purposes under discussion because of their low tension, bending, reverse bending, and long-term creep properties.

U.S. application Ser. No. 923,934, filed July 13, 1978 now U.S. Pat. No. 4,268,468, Esper et al. assigned to the assignee of this application, discloses devices comprising a fiber reinforced thermoset plastic core as the support element and a biologically compatible surface layer of polyethylene. Polyethylene has been considered the resin material having the best biological compatibility with the human body. However, it has been found by lengthy experiments that when implanted in the body for long periods of time, polyethylene does not have such favorable biological compatibility as has been assumed. Primarily with regard to the coalescence of the surface of the polyethylene with the bone, it has been discovered that frequently a more or less thick layer of connective tissue is formed on the polyethylene surface which is considered another cause for the implant later becoming loose.

It is an object of the invention to provide prosthetic devices suitable for implants which have improved long-term biological compatibility and which coalesce with the bone tissue adjacent the implant without the formation of an intermediate layer.

THE INVENTION

The present invention provides prosthetic devices for use as implants in the human body having a core or substrate portion and a surface portion both of which are fiber reinforced characterized by utilizing a triazine resin as the resin for the surface portion of the implant, and preferably also for the core.

The implant is preferably reinforced with carbon fibers or other high strength fibers having a high modulus of elasticity. It is preferred that the reinforcing material should be in the form of one or more fabrics, webs, produced from fibers. Alternately the reinforcing material should be a combination of one or more webs together with fibers in the form of stands.

The reinforcing materials comprise fibers in dissimilar orientation.

The implants of the present invention are generally in the form of prosthesis intended for implantation or in the form of elements such as plates or pins or rods intended to support or connect elements of the body.

The medical prosthesis of the present invention has the advantage that when implanted in the human body after a period of twelve months, no disadvantages with respect to biological compatability have become apparent. There appears to be complete coalescence (growth) of the bone tissue with the adjacent implant, without the formation of an intermediate layer. The utilization of the triazine resins has the advantage that when reinforced with fibers, particularly carbon fibers, it is possible to produce a high strength material and at the time a material whose strength can be adjusted to the desired degree. This is particularly suitable for medical prosthesis intended to be implanted into the body, and particularly hip joint prostheses. Such prostheses have the additional biomechanical advantages in that they are readily adapted to the rigidity of the bone and they may be shaped in such a fashion that harmful stresses upon the bone leading to decomposition are not created.

Triazine resins, a species of cyanate resins, when reinforced with fibers having been disclosed as the core or substrate materials in the prosthetic devices disclosed in application Ser. No. 923,934 which issued as U.S. Pat. No. 4,268,468. It was at that time the prevailing opinion among experts that such a synthetic resin which is a thermoset resin would not exhibit satisfactory biological compatability for use as a surface material because thermoset resins could always give off substances which would result in an unsatisfactory biological compatability with the human body. Surprisingly, it has been discovered that this commonly prevailing prejudice against using thermosetting plastics in general and against using triazine resins in particular is wrong, and that fiber reinforced triazine resins and particularly carbon fiber reinforced triazine resin prostheses devices have excellent biological compatability with the human body. In a particularly preferred embodiment of the present invention the reinforcing material comprises one or more webs of carbon fibers in which the fibers are of dissimilar orientation. This particularly preferred embodiment is a medical prosthesis having mechanical characteristics which have an excellent match to the characteristics of bone and, therefore, particularly suitable for use as an implant in contact with the human or other mammal bone structure.

The invention will be described by way of example with reference to the accompanying drawings, wherein.

Figure 1:
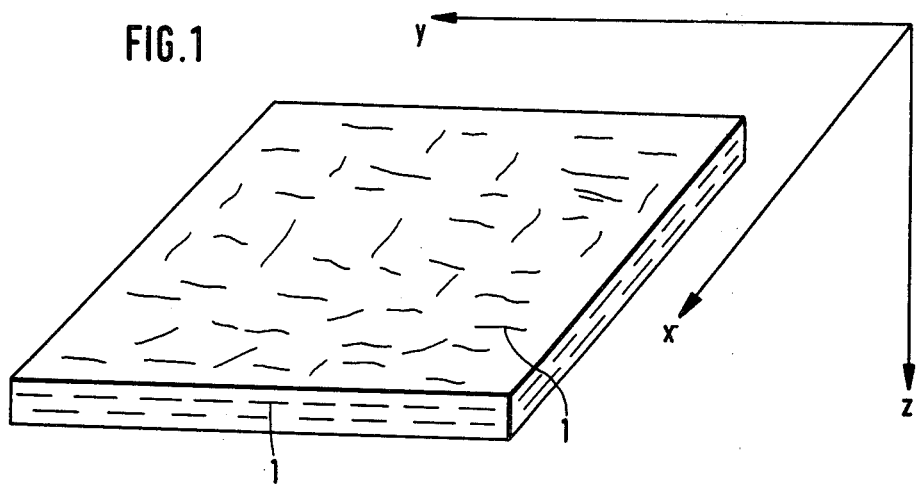
FIG. 1 is a schematic picture of the alignement of the fibers in a fabric with the three directions in the space x, y and z.

A web according to FIG. 1 comprises layers of carbon fibers 1. The fibers in a layer are aligned to a portion of more than 65% in the y-direction, more than 30% in the x-direction and less than 5% in the z-direction, i.e. the web shows mainly a two-dimensional orientation.

Figure 2:
FIG. 2 is a schematic cross-sectional view through a portion of a prosthesis, for example, for use as a bone replacement, and illustrating one embodiment of the present invention.

The prosthesis according to FIG. 2 can comprise only webs (fabric) 10 according to FIG. 1 or may be built up by webs 10 and layers of parallelly arranged carbon fibers 12 according to FIG. 2 or in a random sequence for satisfying the mechanical strength requirements.

These arrangements are impregnated with liquid triazine resin which is a highly heat resistant thermosetting resin of addition polymerization type with functional group Ar$-$($-$O$-$C$\equiv$N$)_n$ as described in the brochure: "High Heat Resistant Resin—BT Resin (Bismaleimide Triazine)", edited by Mitsubishi Gas Chemical Company, Inc. in 1979. These triazine resins contain the triazine ring

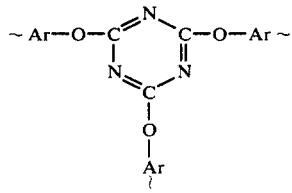

formed by setting of the resin by heating.

The liquid triazine resin is for example a Triazin A (marketed by Bayer A. G.) dissolved in acetone (70% by weight resin dissolved in 30% by weight acetone). The web is then rolled together and preformed in the form of a rough outline of the molded prosthesis which will be produced. The preformed soaked (impregnated) web is then inserted into a mold, preferably a two-part mold. The overall volume of the preformed element is usually somewhat greater than the volume of the mold when completely closed. The mold, therefore, must have an opening from which excess resin can escape when the two-part mold is compressed. The mold with the preformed material therein is heated to about 160° C. and then the two-part mold is compressed and the resin is cured, i.e. the resin sets. After cooling, the cured prosthesis is removed from the mold having a surface as well as a substrate formed from the carbon fiber reinforced triazine resin. The said reinforced triazine prosthesis has a bending strength of over 600 N/mm$^2$ and an modulus of elasticity of between 50,000 and 100,000 N/mm$^2$. By varying the length of the fibers and the fiber orientation in the web, physical characteristics of the implant can be matched with those of the intended bone material. It is possible to vary the desired mechanical properties over a wide range.

We claim:

1. Medical prosthesis suitable for implant use comprising a cured fiber reinforced resin body, said body having a substrate portion and a surface portion and at least said surface portion comprises a triazine resin; said triazine resin being a set liquid triazine thermosetting resin of addition polymerization type having the functional group Ar$-$($-$O$-$C$\equiv$N$)_n$ which has been set by heating to form the triazine ring

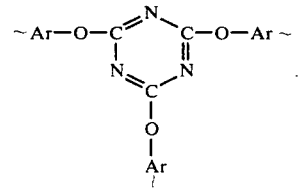

2. The prosthesis of claim 1 wherein said fibers are carbon fibers.

3. The prosthesis of claim 1 or 2 wherein said fibers are formed into a fabric which is used to reinforce said resin.

4. The prosthesis of claim 1 or 2 wherein said resin is reinforced by a combination of fabric material and fibers in the form of strands.

5. The prosthesis of claim 3 wherein the fibers forming the fabric material are in a two dimensional orientation.

6. The prosthesis of claim 4 wherein the fibers forming the fabric material are in a two dimensional orientation.

7. The prosthesis of claim 6 having a bending strength in excess of 600 N/mm$^2$ and an modulus of elasticity of between 50,000 and 100,000 N/mm$^2$.

8. The prosthesis of claim 5 having a bending strength in excess of 600 N/mm$^2$ and an modulus of elasticity of between 50,000 and 100,000 N/mm$^2$.

9. The prosthesis of claim 1 wherein said triazine resin comprises substantially all of the resin component of said cured fiber reinforced resin body.

* * * * *